(12) United States Patent
Ghosh

(10) Patent No.: US 10,653,886 B2
(45) Date of Patent: May 19, 2020

(54) DELIVERY OF LEFT VENTRICULAR PACING THERAPY DURING CARDIAC RESYNCHRONIZATION THERAPY IN A CARDIAC MEDICAL DEVICE AND MEDICAL DEVICE SYSTEM

(71) Applicant: Medtronic, Inc., Minneapolis, MN (US)

(72) Inventor: Subham Ghosh, Blaine, MN (US)

(73) Assignee: Medtronic Inc., Minneapolis, MN (US)

( * ) Notice: Subject to any disclaimer, the term of this patent is extended or adjusted under 35 U.S.C. 154(b) by 678 days.

(21) Appl. No.: 15/222,302

(22) Filed: Jul. 28, 2016

(65) Prior Publication Data

US 2017/0028202 A1 Feb. 2, 2017

Related U.S. Application Data

(60) Provisional application No. 62/199,409, filed on Jul. 31, 2015, provisional application No. 62/199,424, filed on Jul. 31, 2015.

(51) Int. Cl.
*A61N 1/37* (2006.01)
*A61B 5/042* (2006.01)
(Continued)

(52) U.S. Cl.
CPC .......... *A61N 1/3684* (2013.01); *A61B 5/0456* (2013.01); *A61B 5/0468* (2013.01);
(Continued)

(58) Field of Classification Search
CPC .......... A61N 1/37; A61N 1/365; A61N 1/368; A61N 1/375; A61N 1/362; A61B 5/042
(Continued)

(56) References Cited

U.S. PATENT DOCUMENTS 5,193,550 A 3/1993 Duffin
5,354,316 A 10/1994 Keimel
(Continued)

OTHER PUBLICATIONS

U.S. Appl. No. 14/695,111, filed Apr. 24, 2015.
(Continued)

*Primary Examiner* — Jon Eric C Morales
(74) *Attorney, Agent, or Firm* — Mueting Raasch Group

(57) ABSTRACT

A medical device and medical device system for delivering left ventricular pacing that includes a subcutaneous sensing device having a subcutaneous electrode to sense a subcutaneous cardiac signal and an emitting device to emit a trigger signal in response to the sensed cardiac signal, an intracardiac therapy delivery device to deliver the left ventricular pacing in response to the emitted trigger signal, and a processor configured to determine whether the medical device system is in one of a VVD pacing mode and a VVI pacing mode, determine whether the delivered left ventricular pacing captures the left ventricle, determine whether to adjust a pacing parameter in response to the determination of whether the device system is in one of a VVD pacing mode and a VVI pacing mode and the determination of whether the delivered left ventricular pacing captures the left ventricle, and deliver the left ventricular pacing in response to determining whether to adjust the pacing parameter.

13 Claims, 7 Drawing Sheets

(51) Int. Cl.
  *A61N 1/368* (2006.01)
  *A61N 1/365* (2006.01)
  *A61N 1/375* (2006.01)
  *A61B 5/0452* (2006.01)
  *A61B 5/0456* (2006.01)
  *A61B 5/0468* (2006.01)
  *A61N 1/372* (2006.01)
  *A61N 1/05* (2006.01)
  *A61N 1/39* (2006.01)
  *A61B 5/00* (2006.01)
  *A61N 1/362* (2006.01)

(52) U.S. Cl.
  CPC .......... *A61B 5/04525* (2013.01); *A61N 1/056* (2013.01); *A61N 1/3682* (2013.01); *A61N 1/3688* (2013.01); *A61N 1/36514* (2013.01); *A61N 1/371* (2013.01); *A61N 1/3712* (2013.01); *A61N 1/3756* (2013.01); *A61N 1/37223* (2013.01); *A61N 1/3956* (2013.01); *A61B 5/042* (2013.01); *A61B 5/4836* (2013.01); *A61N 1/3627* (2013.01)

(58) Field of Classification Search
  USPC .............................................. 607/17, 27, 28
  See application file for complete search history.

(56) References Cited

U.S. PATENT DOCUMENTS

| | | |
|---|---|---|
| 5,545,186 A | 8/1996 | Olson et al. |
| 5,601,615 A | 2/1997 | Markowitz et al. |
| 5,683,431 A | 11/1997 | Wang |
| 5,702,427 A | 12/1997 | Ecker et al. |
| 5,843,137 A | 12/1998 | Condie et al. |
| 5,855,593 A | 1/1999 | Olson et al. |
| 5,861,012 A | 1/1999 | Stroebel |
| 5,861,013 A | 1/1999 | Peck et al. |
| 5,871,512 A | 2/1999 | Hemming et al. |
| 5,873,898 A | 2/1999 | Hemming et al. |
| 5,902,325 A | 5/1999 | Condie et al. |
| 5,954,756 A | 9/1999 | Hemming et al. |
| 6,134,473 A | 10/2000 | Hemming et al. |
| 6,144,881 A | 11/2000 | Hemming et al. |
| 6,163,724 A | 12/2000 | Hemming et al. |
| 6,216,037 B1 | 4/2001 | Van Oort |
| 6,249,702 B1 | 6/2001 | Van Oort |
| 6,393,316 B1 | 5/2002 | Gillberg et al. |
| 6,434,428 B1 | 8/2002 | Sloman et al. |
| 6,477,422 B1 | 11/2002 | Splett |
| 6,658,293 B2 | 12/2003 | Vonk |
| 7,027,868 B2 | 4/2006 | Rueter et al. |
| 7,130,690 B2 | 10/2006 | Rueter et al. |
| 7,139,610 B2 | 11/2006 | Ferek Petric |
| 7,142,928 B2 | 11/2006 | Sharma et al. |
| 7,177,680 B2 | 2/2007 | Sharma et al. |
| 7,280,868 B2 | 10/2007 | Rueter et al. |
| 7,317,943 B2 | 1/2008 | Ferek Petric |
| 7,400,924 B2 | 7/2008 | Rueter |
| 7,433,736 B2 | 10/2008 | Rueter et al. |
| 7,555,336 B2 | 6/2009 | Sheth et al. |
| 7,561,914 B2 | 7/2009 | Busacker et al. |
| 7,684,863 B2 | 3/2010 | Parikh et al. |
| 7,742,812 B2 | 6/2010 | Ghanem et al. |
| 7,783,355 B2 | 8/2010 | Rueter |
| 7,787,942 B2 | 8/2010 | Chinchoy et al. |
| 7,818,059 B2 | 10/2010 | Rueter et al. |
| 7,831,303 B2 | 11/2010 | Rueter et al. |
| 7,904,153 B2 | 3/2011 | Greenhut et al. |
| 7,941,217 B1 | 5/2011 | Pei et al. |
| 8,160,684 B2 | 4/2012 | Ghanem et al. |
| 8,417,337 B2 | 4/2013 | Busacker et al. |
| 8,527,050 B2 | 9/2013 | Stadler et al. |
| 8,532,785 B1 | 9/2013 | Crutchfield et al. |
| 8,615,298 B2 | 12/2013 | Ghosh et al. |
| 8,620,433 B2 | 12/2013 | Ghosh et al. |
| 8,626,291 B2 | 1/2014 | Stadler et al. |
| 8,718,769 B2 | 5/2014 | Hilpisch et al. |
| 8,718,770 B2 | 5/2014 | Demmer et al. |
| 8,738,131 B2 | 5/2014 | Chinchoy et al. |
| 8,738,132 B1 | 5/2014 | Ghosh et al. |
| 8,744,579 B2 | 6/2014 | Parikh et al. |
| 8,750,998 B1 | 6/2014 | Ghosh et al. |
| 8,750,999 B1 | 6/2014 | Ghosh et al. |
| 8,768,465 B2 | 7/2014 | Ghosh et al. |
| 8,781,584 B2 | 7/2014 | Demmer et al. |
| 8,886,307 B2 | 11/2014 | Sambelashvili et al. |
| 8,923,963 B2 | 12/2014 | Bonner et al. |
| 8,929,984 B2 | 1/2015 | Ghosh et al. |
| 8,948,869 B2 | 2/2015 | Ghosh et al. |
| 9,002,454 B2 | 4/2015 | Ghosh et al. |
| 9,061,157 B2 | 6/2015 | Ghosh et al. |
| 9,656,087 B2* | 5/2017 | Ghosh ................ A61N 1/37223 |
| 2005/0131478 A1* | 6/2005 | Kim .................... A61B 5/7217 607/27 |
| 2006/0136002 A1 | 6/2006 | Sheth et al. |
| 2006/0155338 A1 | 7/2006 | Mongeon et al. |
| 2006/0161207 A1 | 7/2006 | Busacker et al. |
| 2009/0163973 A1 | 6/2009 | Meyer et al. |
| 2009/0276001 A1 | 11/2009 | Busacker et al. |
| 2010/0137935 A1 | 6/2010 | Parikh et al. |
| 2011/0178567 A1 | 7/2011 | Pei et al. |
| 2013/0079861 A1 | 3/2013 | Reinert et al. |
| 2013/0090702 A1 | 4/2013 | Mongeon et al. |
| 2014/0107723 A1 | 4/2014 | Hou et al. |
| 2014/0121720 A1 | 5/2014 | Bonner et al. |
| 2015/0321011 A1 | 11/2015 | Carney et al. |
| 2015/0321012 A1 | 11/2015 | Cinbis et al. |
| 2016/0144190 A1 | 5/2016 | Cao et al. |
| 2017/0028206 A1* | 2/2017 | Ghosh ................ A61N 1/37223 |

OTHER PUBLICATIONS (PCT/US2016/044658) PCT Notification of Transmittal of the International Search Report and the Written Opinion of the International Searching Authority, dated Oct. 24, 2016, 12 pages.

(PCT/US2016/044681) PCT Notification of Transmittal of the International Search Report and the Written Opinion of the International Searching Authority, dated Oct. 27, 2016, 13 pages.

* cited by examiner

DELIVERY OF LEFT VENTRICULAR PACING THERAPY DURING CARDIAC RESYNCHRONIZATION THERAPY IN A CARDIAC MEDICAL DEVICE AND MEDICAL DEVICE SYSTEM

CROSS-REFERENCE TO RELATED APPLICATIONS

This application claims the benefit of U.S. Provisional Application Nos. 62/199,409 and 62/199,424, both of which were filed on Jul. 31, 2015. The disclosure of the above applications are incorporated herein by reference in their entirety.

FIELD OF THE DISCLOSURE

The present disclosure pertains to cardiac pacing methods and systems, and, more particularly, to delivery of left ventricular pacing during cardiac resynchronization therapy in a cardiac medical device and medical device system.

BACKGROUND OF THE DISCLOSURE

Implantable pacemakers and cardioverter defibrillators (ICDs) are available for delivering electrical stimulation therapies to a patient's heart, such as bradycardia pacing, cardiac resynchronization therapy (CRT), anti-tachycardia pacing and cardioversion/defibrillation shocks. Medical device technology advancement has led toward smaller and smaller implantable devices. Recently, this reduction in size has resulted in the introduction of leadless intracardiac pacemakers that can be implanted directly in a heart chamber. One advantage of a leadless intracardiac device is the elimination of the use of transvenous, intracardiac leads, resulting in the elimination of complications due to infection associated with a lead extending from a subcutaneous pacemaker pocket transvenously into the heart, for example. Other complications such as "twiddler's syndrome", lead fracture or poor connection of the lead to the pacemaker are eliminated as the result of the use of a leadless, intracardiac pacemaker.

New challenges arise, however, in controlling an intracardiac pacemaker to deliver pacing pulses in synchrony with paced or sensed events occurring in other heart chambers. Cardiac resynchronization therapy (CRT) is an example of a pacing therapy that includes delivering pacing pulses in a heart chamber at a predetermined time interval after a sensed or paced event in another heart chamber. CRT is a treatment for heart failure patients in whom one or more heart chambers are electrically paced to restore or improve heart chamber synchrony. Improved heart chamber synchrony is expected to alleviate symptoms of heart failure. Achieving a positive clinical benefit from CRT, however, may be dependent on several therapy control parameters, such as the timing intervals used to control pacing pulse delivery, e.g., an atrio-ventricular (AV) interval and/or an inter-ventricular (VV) interval. The AV interval controls the timing of ventricular pacing pulses relative to a preceding atrial depolarization, intrinsic or paced. The VV interval controls the timing of a pacing pulse in one ventricle relative to a paced or intrinsic sensed event in the other ventricle. Pacing may be delivered in the right ventricle (RV) and/or the left ventricle (LV) to restore ventricular synchrony.

Cardiac resynchronization utilizing cardiac ventricular pacing therapy and cardiac pacing devices operate by either delivering pacing stimulus to both ventricles or to one ventricle with the desired result of a more or less simultaneous mechanical contraction and ejection of blood from the ventricles. Triggered pacing systems have been developed for delivery of cardiac synchronization therapy, such as described, for example, in U.S. Patent Application Publication No. 2015-0321011 A1, to Carney et al. Such triggered pacing systems may include a therapy delivery device, such as a pacing device implanted with the left ventricle, that delivers the ventricular pacing therapy and a sensing device, such as a subcutaneously position implantable cardio-defibrillator (ICD), that senses a physiological signal to determine a need for therapy, and generate a control signal passed to a trigger signal emitting device when therapy delivery by the therapy delivery device is required. The trigger signal emitting device emits a trigger signal that is detected by the therapy delivery device, which then delivers at least a portion of a CRT therapy to the patient.

Ideally, each pacing pulse stimulus delivered to a ventricle evokes a response from the ventricle. The verification of capture of the left ventricle and delivery of effective left ventricular pacing help to ensure that the desired evoked response takes place during delivery of ventricular pacing therapy, and is therefore is an important factor in the delivery of ventricular pacing therapy for cardiac resynchronization therapy (CRT).

DETAILED DESCRIPTION OF EXEMPLARY EMBODIMENTS

In the following detailed description, references are made to illustrative embodiments for carrying out methods of delivering atrial synchronous pacing with sensing of atrial activity from subcutaneous or far-field signals reflecting electrical activity of the different heart chambers. It is understood that other embodiments may be utilized without departing from the scope of the invention. For example, the invention is disclosed in detail herein in the context of a bi-ventricular or multi-electrode/multi-site cardiac resynchronization therapy (CRT) delivery.

Exemplary methods, devices, and systems shall be described with reference to FIGS. 1-6. It will be apparent to one skilled in the art that elements or processes from one embodiment may be used in combination with elements or processes of the other embodiments, and that the possible embodiments of such methods, devices, and systems using combinations of features set forth herein is not limited to the specific embodiments shown in the Figures and/or described herein. Further, it will be recognized that the embodiments described herein may include many elements that are not necessarily shown to scale.

Figure 1:
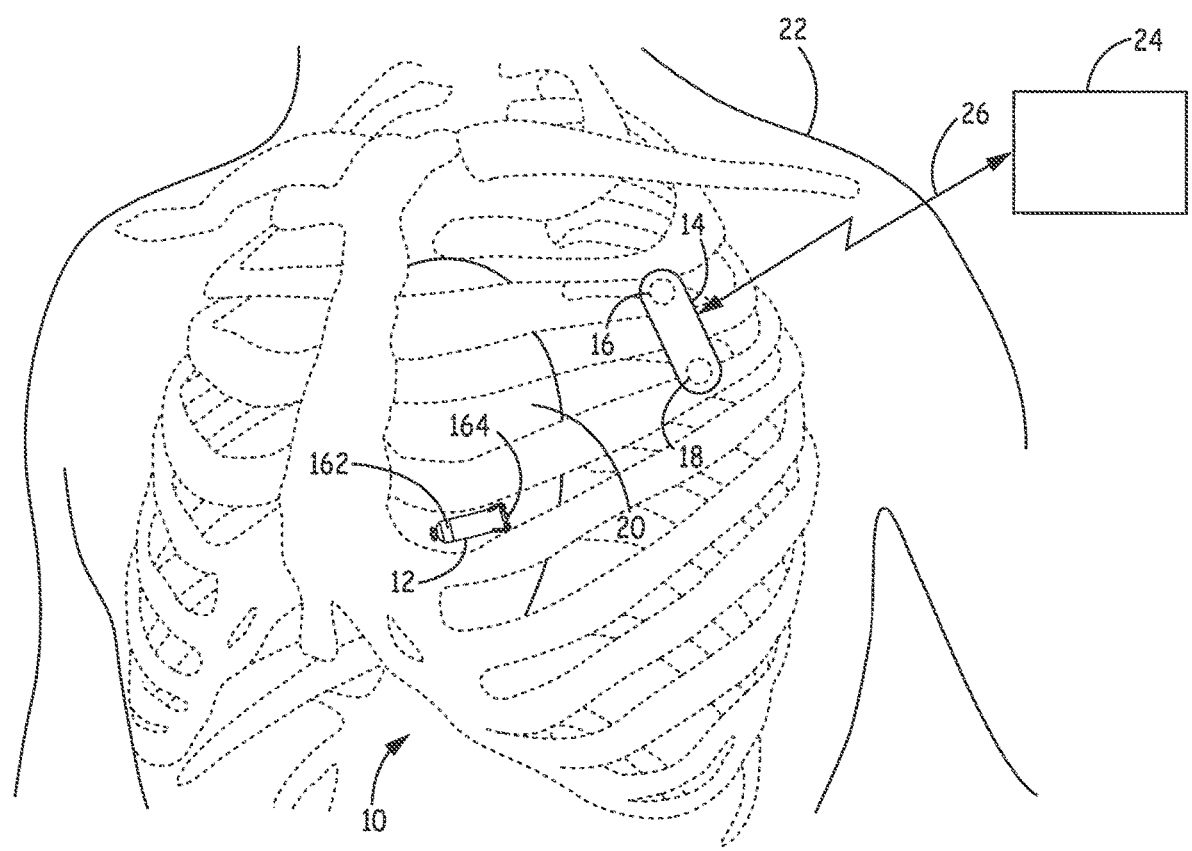
FIG. 1 is a conceptual diagram illustrating an exemplary implantable medical device (IMD) system for delivering left ventricular pacing during cardiac resynchronization therapy according to an embodiment of the present disclosure.

FIG. 1 is a conceptual diagram illustrating an exemplary implantable medical device (IMD) system for delivering left ventricular pacing during cardiac resynchronization therapy according to an embodiment of the present disclosure. As illustrated in FIG. 1, according to one embodiment, an implantable medical device (IMD) system 10 for delivering resynchronization pacing therapy may include a therapy delivery device 12, such as an intracardiac pacemaker, and a cardiac sensing device 14, such as an ECG monitor, having a pair of housing-based electrodes 16 and 18 for sensing an ECG signal positioned along a housing of the cardiac sensing device 14. For example, as illustrated in FIG. 1, according to one embodiment, the therapy delivery device 12 may be embodied as a leadless pacing device or pacemaker positioned within the left ventricle of a heart 20 of a patient 22 and capable of delivering pacing therapy, such as cardiac resynchronization therapy, for example, to the left ventricle of the heart 20, and the cardiac sensing device 14 may be embodied as a subcutaneous monitoring device that may be subcutaneously implanted to be positioned at one of a variety of locations that facilitate a trigger signal transmission from an emitting device (shown in FIG. 2) located along the sensing device 14 and facing towards the therapy delivery device 12 to be received by the therapy delivery device 12 without requiring a lead-based or leadless emitting device spaced apart from the sensing device 14. Such a system is described, for example, in U.S. Patent Publication No. 2015-0321011 A1, to Carney et. al, incorporated herein by reference in it's entirety.

It is understood that while the sensing device is described as being a subcutaneously positioned leadless monitoring device, other devices may also be used if desired, such as a subcutaneously implantable ICD, as described, for example, in U.S. Patent Publication No. 2015-0321011 A1, to Carney et al., incorporated herein by reference in it's entirety. In another embodiment, the sensing device may be a subcutaneously implanted leadless device, such as the leadless subcutaneous sensor device in commonly assigned U.S. Patent Application Nos. 2015-0321011 A1 to Carney. al, and US 2015-0321012 A1 to Cinbis et. al, for example, both incorporated by reference in their entireties.

FIG. 1 further depicts a programmer 24 in wireless communication with cardiac sensing device 14 via a communication link 26. In some examples, programmer 24 comprises a handheld computing device, computer workstation, or networked computing device. Programmer 24 includes a user interface that presents information to and receives input from a user. It should be noted that the user may also interact with programmer 24 remotely via a networked computing device.

A user, such as a physician, technician, surgeon, electrophysiologist, other caregiver, or patient, may interact with programmer 24 to communicate with cardiac sensing device 14. For example, the user may interact with programmer 24 to retrieve physiological or diagnostic information from cardiac sensing device 14. A user may also interact with programmer 24 to program cardiac sensing device 14, e.g., select values for operational parameters of the cardiac sensing device 14, including parameters used to control a trigger emitting device positioned along the sensing device 14 to emit a trigger signal for controlling therapy delivery device 12. A user may use programmer 24 to retrieve information from cardiac sensing device 14 regarding the rhythm of heart 20, heart rhythm trends over time, or arrhythmic episodes.

As indicated, cardiac sensing device 14 and programmer 24 communicate via wireless communication 26. Examples of communication techniques may include low frequency or radiofrequency (RF) telemetry, but other techniques may be used. In some examples, programmer 24 may include a programming head that is placed proximate to the patient's body near the cardiac sensing device 14 implant site in order to improve the quality or security of communication between cardiac sensing device 14 and programmer 24.

Figure 2:
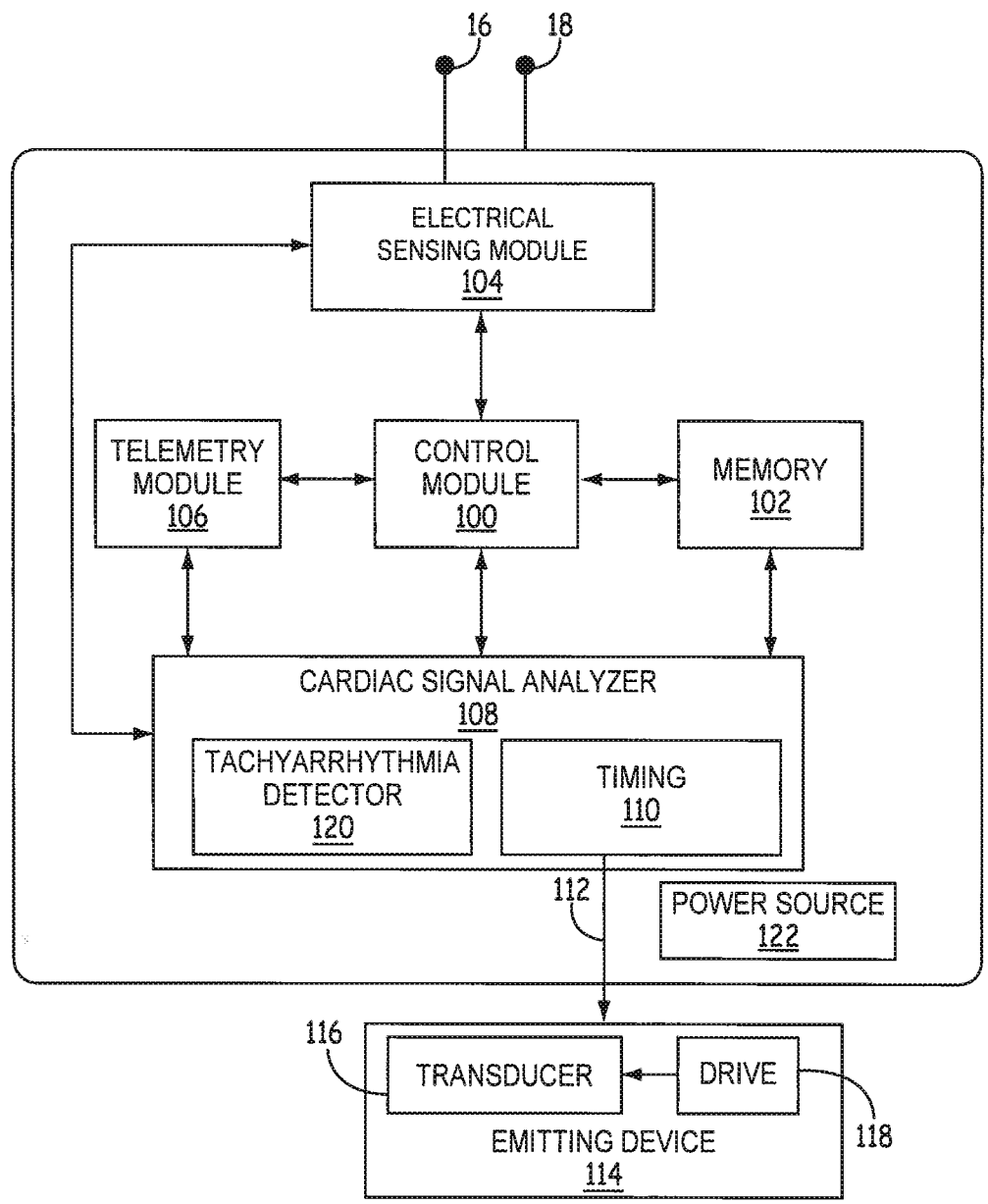
FIG. 2 is a functional block diagram of an exemplary sensing device of the implantable medical device (IMD) system of FIG. 1.

FIG. 2 is a functional block diagram of an exemplary sensing device of the implantable medical device (IMD) system of FIG. 1. As illustrated in FIG. 2, the sensing device 14 includes processing and control module 100, also referred to as "control module" 100, a memory 102, an electrical sensing module 104, a telemetry module 106, and cardiac signal analyzer 108. A power source 122 provides power to the circuitry of the sensing device 14, including each of the modules 100-108. Power source 122 may include one or more energy storage devices, such as one or more chargeable or non-re-chargeable batteries.

The functional blocks shown in FIG. 2 represent functionality that may be included in sensing device 14 and may include any discrete and/or integrated electronic circuit components that implement analog and/or digital circuits capable of producing the functions attributed to sensing device 14 herein. For example, the modules may include analog circuits, e.g., amplification circuits, filtering circuits, and/or other signal conditioning circuits. The modules may also include digital circuits, e.g., analog-to-digital converters, combinational or sequential logic circuits, integrated circuits, memory devices, etc. Memory 102 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), flash memory, or any other memory device. Furthermore, memory 102 may include non-transitory computer readable media storing instructions that, when executed by one or more processing circuits, cause control module 100 or other ICD modules to perform various functions attributed to sensing device 14. The non-transitory computer readable media storing the instructions may include any of the media listed above, with the sole exception being a transitory propagating signal. The particular form of software, hardware and/or firmware employed to implement the functionality disclosed herein will be determined primarily by the particular system architecture employed in the IMD system devices. Providing software, hardware, and/or firmware to accomplish the described functionality in the context of any modern IMD system, given the disclosure herein, is within the abilities of one of skill in the art.

The functions attributed to the modules herein may be embodied as one or more processors, hardware, firmware, software, or any combination thereof. Depiction of different features as modules is intended to highlight different functional aspects and does not necessarily imply that such modules must be realized by separate hardware or software components. Rather, functionality associated with one or more modules may be performed by separate hardware or software components, or integrated within common hardware or software components. For example, arrhythmia detection operations performed by cardiac signal analyzer 108 for determining a need for therapy delivered by sensing device 14 and/or therapy delivery device 12 may be implemented in processing and control module 100 executing instructions stored in memory 102.

Processing and control module 100 communicates with cardiac signal analyzer 108 and electrical sensing module 104 for sensing cardiac electrical activity, detecting cardiac rhythms, and generating cardiac therapies in response to sensed signals. Sensing module 14 includes one or more sense amplifiers or other cardiac event detection circuitry for sensing cardiac events, e.g., P-waves or R-waves, from the ECG signal(s). Sensing module 14 passes sense event signals to cardiac signal analyzer 108 in response to sensing cardiac events. For example P-wave sense event signals and R-wave sense event signals are passed to cardiac signal analyzer 108 when the ECG signal crosses a respective P-wave sensing threshold and R-wave sensing threshold, which may each be auto-adjusting sensing thresholds. Bradycardia or asystole is typically determined by a pacing escape interval timer expiring within the timing circuit 110. In response to the pacing escape interval expiring, a control signal 112 is passed to a trigger signal emitting device 114. The pacing escape interval is restarted upon a trigger signal or a sense event signal.

The control signal 112 in the illustrative examples presented herein may be referred to as a pacing control signal because it causes therapy delivery device 12 to deliver a cardiac resynchronization pacing pulse to a heart chamber. In other examples, the control signal 112 may be produced by cardiac signal analyzer 108 to cause other types of therapy pulses to be delivered by therapy delivery device 12 (or another therapy delivery device). For example control signal 112 may be produced to cause therapy delivery device 12 or another therapy delivery device to deliver an ATP pulse, a vagal nerve stimulation pulse, or other type of electrical stimulation pulse.

Trigger signal emitting device 114 includes a drive signal circuit 118 that receives the control signal 112, either as a wired electrical signal or a wireless signal from telemetry module 106. Drive signal circuit 118 passes an electrical signal to transducer 116 to enable transducer 116 to emit the trigger signal. Transducer 116 may be an optical transducer or an acoustical transducer in various examples. In other examples, the drive signal circuit 118 is coupled to an antenna for transmitting the trigger signal as an RF signal.

The trigger signal is received and detected by therapy delivery device 12 causing therapy delivery device 12 to deliver one or more pacing pulses to the patient's heart. In some examples, the trigger signal is generated according to predetermined frequency, amplitude, duration and other characteristics that are not intentionally varied by emitting device 114 under the control signal 112. In other words, the trigger signal merely signals therapy delivery device 12 to deliver therapy without any information relating to how many pacing pulses, what pulse amplitude or pulse width or other pacing pulse control parameters. Therapy delivery device 12 is programmed to deliver a predetermined number of pacing pulses according to predefined pulse control parameters when the trigger signal is detected.

Alternatively, control signal 112 may include encoded pacing pulse control information. The control signal 112 generated by drive circuit 118 may cause transducer 116 to emit a trigger signal according to a frequency, duration, amplitude or other intentionally varied characteristics of the trigger signal to include pacing pulse control parameter information. As described below, a parameter of the trigger signal emitted by transducer 116 may be controllably varied by control signal 112 and drive circuit 118 to cause therapy delivery device 12 to adjust a pacing pulse control parameter such as pacing pulse width, pulse number, etc. Trigger signal parameters that may be varied under the control of signal 112 and drive circuit 118 include, without limitation, trigger signal amplitude, signal frequency, pulse width, pulse number and interpulse interval.

Transducer 116 may be embodied as one or more transducers configured to emit sound or light, for example, upon receiving a drive signal from circuit 118. Transducer 116 may include any combination of one or more of a ceramic piezoelectric crystal, a polymer piezoelectric crystal, capacitive micromachined ultrasonic transducer (CMUT), piezoelectric micromachined ultrasonic transducer (PMUT), or other ultrasonic transducer, a light emitting diode (LED), a vertical cavity surface emitting laser (VCSEL) or other light source having a high quantum efficiency at a selected light wavelength. Transducer 116 may include multiple transducers arranged in an array and/or configured to emit signals in multiple directions from emitting device 114 to promote reception of the trigger signal by therapy delivery device 12 despite shifting, rotation or other changes of the relative orientations of emitting device 114 and therapy delivery device 12 with respect to each other. The multiple transducers may be selectable by drive circuit 118 such that a single one or combination of transducers producing the best signal-to-noise ratio at the pacemaker receiving transducer is selected.

The transducer 116 is configured to emit a trigger signal at an amplitude and frequency that is detectable by a receiving transducer of therapy delivery device 100, after attenuation by body tissues along the pathway between the transducer 36 and the therapy delivery device 12. In one example, transducer 116 is configured to emit sounds in the range of approximately 40 kHz to over 1 MHz. An optical trigger signal may be emitted with a wavelength greater than approximately 1000 nm. An RF signal can be radiated from an antenna at frequencies between 400 MHz and 3 GHz. The frequency of the trigger signal is selected in part based on the types and thicknesses of body tissues encountered along the signal pathway.

Timing circuit 110 may generate control signal 112 to trigger therapy delivery device 12 to provide bradycardia pacing, anti-tachycardia pacing, cardiac resynchronization therapy, AV nodal stimulation, or other pacing therapies according to pacing algorithms and timing intervals stored in memory 102. Cardiac signal analyzer 108 may include a tachyarrhythmia detector 120 for detecting and discriminating supraventricular tachycardia (SVT), ventricular tachycardia (VT) and ventricular fibrillation (VF). Some aspects of sensing and processing subcutaneous ECG signals are generally disclosed in commonly-assigned U.S. Pat. No. 7,904,153 (Greenhut, et al.), and in U.S. patent application Ser. No. 14/695,111 (Sarkar et. al.), both of which are hereby incorporated herein by reference in their entireties. The timing of R-wave sense event signals from sensing module 104 is used by tachyarrhythmia detector 120 to measure R-R intervals for counting RR intervals in different detection zones or determining a heart rate or other rate-based measurements for detecting ventricular tachyarrhythmia. Electrical sensing module 104 may additionally or alternatively provide digitized ECG signals to cardiac signal analyzer 108 for use in detecting tachyarrhythmia. Examples of ICDs that may be adapted for use with a triggered therapy delivery device 12 and operations that may be performed by tachyarrhythmia detector 120 for detecting, discriminating and treating tachyarrhythmia are generally disclosed in U.S. Pat. No. 7,742,812 (Ghanem, et al.), U.S. Pat. No. 8,160,684 (Ghanem, et al.), U.S. Pat. No. 5,354,316 (Keimel); U.S. Pat. No. 6,393,316 (Gillberg et al.), U.S. Pat. No. 5,545,186 (Olson, et al.), and U.S. Pat. No. 5,855,593 (Olson, et al.), all of which patents are incorporated herein by reference in their entirety.

Telemetry module 106 includes a transceiver and antenna for communicating with another device, such as an external programmer 24 and emitting device 114 when it is configured to receive control signal 112 wirelessly. Under the control of control module 100, telemetry module 106 may receive downlink telemetry from and send uplink telemetry to programmer 24 or another external device. Telemetry module 106 may transmit a control signal wirelessly to emitting device 114, e.g., as an RF signal.

Figure 3:
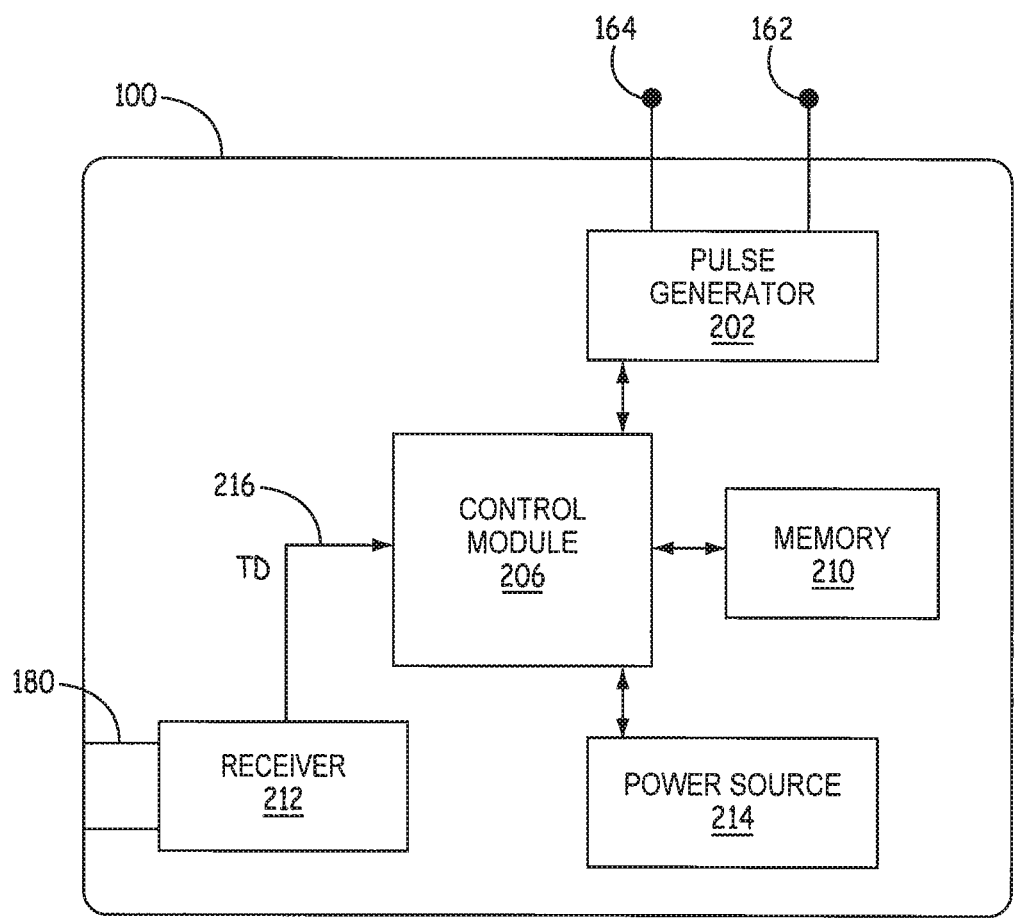
FIG. 3 is a schematic diagram of a therapy delivery device of the implantable medical device (IMD) system of FIG. 1.

FIG. 3 is a schematic diagram of a therapy delivery device of the implantable medical device (IMD) system of FIG. 1. As illustrated in FIG. 3, therapy delivery device 12 includes a pulse generator 202, an optional sensing module (not shown), a control module 206, memory 210, trigger signal receiver 212 and a power source 214. Pulse generator 202 generates electrical stimulation pulses that are delivered to heart tissue via electrodes 162 and 164. Control module 206 controls pulse generator 202 to deliver a stimulation pulse in response to receiving a trigger detect (TD) signal 216 from receiver 212. In other embodiments, pulse generator 202 may be configured to be enabled to deliver a stimulation pulse directly by an input signal received from receiver 212. For example, a switch responsive to a trigger detect signal 216 produced by receiver 212 may enable pulse generator 202 to deliver a stimulation pulse to a targeted tissue via electrodes 162 and 164 (shown in FIG. 1) positioned on the therapy delivery device 12.

Pulse generator 202 includes one or more capacitors and a charging circuit to charge the capacitor(s) to a pacing pulse voltage. The pacing capacitor may be charged to the pacing pulse voltage while control module 206 waits for a trigger detect signal 216 from receiver 212. Upon detecting the trigger signal, the capacitor is coupled to pacing electrodes 162, 164 to discharge the capacitor voltage and thereby deliver the pacing pulse. Alternatively, detection of the trigger signal initiates pacing capacitor charging and when a predetermined pacing pulse voltage is reached, the pulse is delivered. Pacing circuitry generally disclosed in U.S. Pat. No. 8,532,785 (Crutchfield), hereby incorporated herein by reference in its entirety, may be implemented in therapy delivery device 12 for charging a pacing capacitor to a predetermined pacing pulse amplitude under the control of control module 206 and delivering a pacing pulse.

Alternatively, pulse generator 202 may include a switch that connects power source 214 to pacing electrodes 162 and 164 to deliver the pacing pulse. The switch is opened by trigger detect signal 216 or by a control signal from control module 206, and power source 214 delivers energy to pulse generator 202 for generating a pacing pulse.

Control module 206 may determine a pacing pulse control parameter from the trigger detect signal 216 and use the determined pacing pulse control parameter to control pulse generator 202 to deliver one or more pacing pulses in accordance with the determined control parameter. For example, the pulse width or other aspect of the trigger signal may be determined by control module 206 and used to set the pulse width (or another aspect) of the pacing pulse.

Receiver 212 receives trigger signals through coupling member 180. Receiver 212 includes one or more receiving transducers, which may be mounted directly along an inner surface of coupling member 180, e.g., for receiving sound waves or light. The trigger signal causes a receiving transducer to produce a voltage signal that is passed to a comparator included in receiver 212 (or control module 206) for comparison to a trigger signal detection threshold. If the voltage signal produced by the receiving transducer is greater than the detection threshold, a trigger detect signal 216 is passed to control module 206, or directly to pulse generator 202, to cause pacing pulse delivery.

The receiver 212 is configured to detect only the emitting device-generated trigger signal in some embodiments. For example, receiver 212 may be "tuned" to detect an acoustical or optical signal of a particular signal frequency or bandwidth that is outside a normal physiological range of acoustical or optical signal sensing. In some examples, receiver 212 is not configured to sense and process any physiological acoustical signals or optical signals for determining a physiological event, condition or state.

Control module 206 controls pulse generator 202 to deliver a pacing pulse according to therapy delivery control parameters such as pulse amplitude, pulse width, pulse number, etc., which may be stored in memory 210. In some examples, pulse generator 202 is enabled to deliver a pacing pulse immediately upon receiving a trigger detect signal 216, either directly from receiver 212 or via control module 206. Alternatively, the pacing pulse may be delivered after a predetermined time delay.

Receiver 212 may include multiple receiving transducers for sensing the trigger signal. The voltage signal produced by multiple transducers may be summed, for example, for comparison to a trigger signal detection threshold. In some embodiments, multiple receiving transducers may be included that are responsive to different frequency bandwidths. Providing detection of different signal frequencies may enable different trigger signals to be transmitted for causing therapy delivery device 100 to perform different pacing functions and/or improve trigger signal detection.

Power source 214 provides power to each of the other modules and components of pacemaker 100 as required. Control module 206 may execute power control operations to control when various components or modules are powered to perform various pacemaker functions. Power source 214 may include one or more energy storage devices, such as one or more rechargeable or non-rechargeable batteries.

Circuitry represented by the block diagram shown in FIG. 3 may include any discrete and/or integrated electronic circuit components that implement analog and/or digital circuits capable of producing the functions attributed to therapy delivery device 100 herein. The functions attributed to therapy delivery device 100 herein may be embodied as one or more processors, hardware, firmware, software, or any combination thereof. Control module 206 may include any one or more of a microprocessor, a controller, a digital signal processor (DSP), an application specific integrated circuit (ASIC), a field-programmable gate array (FPGA), state machine, or equivalent discrete or integrated logic circuitry. Depiction of different features of therapy delivery device 12 as discrete modules or components is intended to highlight different functional aspects and does not necessarily imply that such modules must be realized by separate hardware or software components. Rather, functionality associated with one or more modules may be performed by separate hardware or software components, or integrated within common or separate hardware or software components, which may include combinational or sequential logic circuits, state machines, memory devices, etc.

Memory 210 may include computer-readable instructions that, when executed by control module 206, cause control module 206 to perform various functions attributed throughout this disclosure to therapy delivery device 12. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal. Memory 210 stores intervals, counters, or other data used by control module 206 to control the delivery of pacing pulses by pulse generator 202 in response to detection of a trigger signal received by receiver 212. Examples of a leadless pacing device may be as described for example in U.S. patent application Ser. No. 13/665,492 to Bonner et al., entitled, "LEADLESS PACEMAKER SYSTEM," and filed on Oct. 31, 2012, or in U.S. patent application Ser. No. 13/665,601 to Bonner et al., entitled, "LEADLESS PACEMAKER SYSTEM," and filed on Oct. 31, 2012, both of which are incorporated herein by reference in their entireties.

Figure 4:
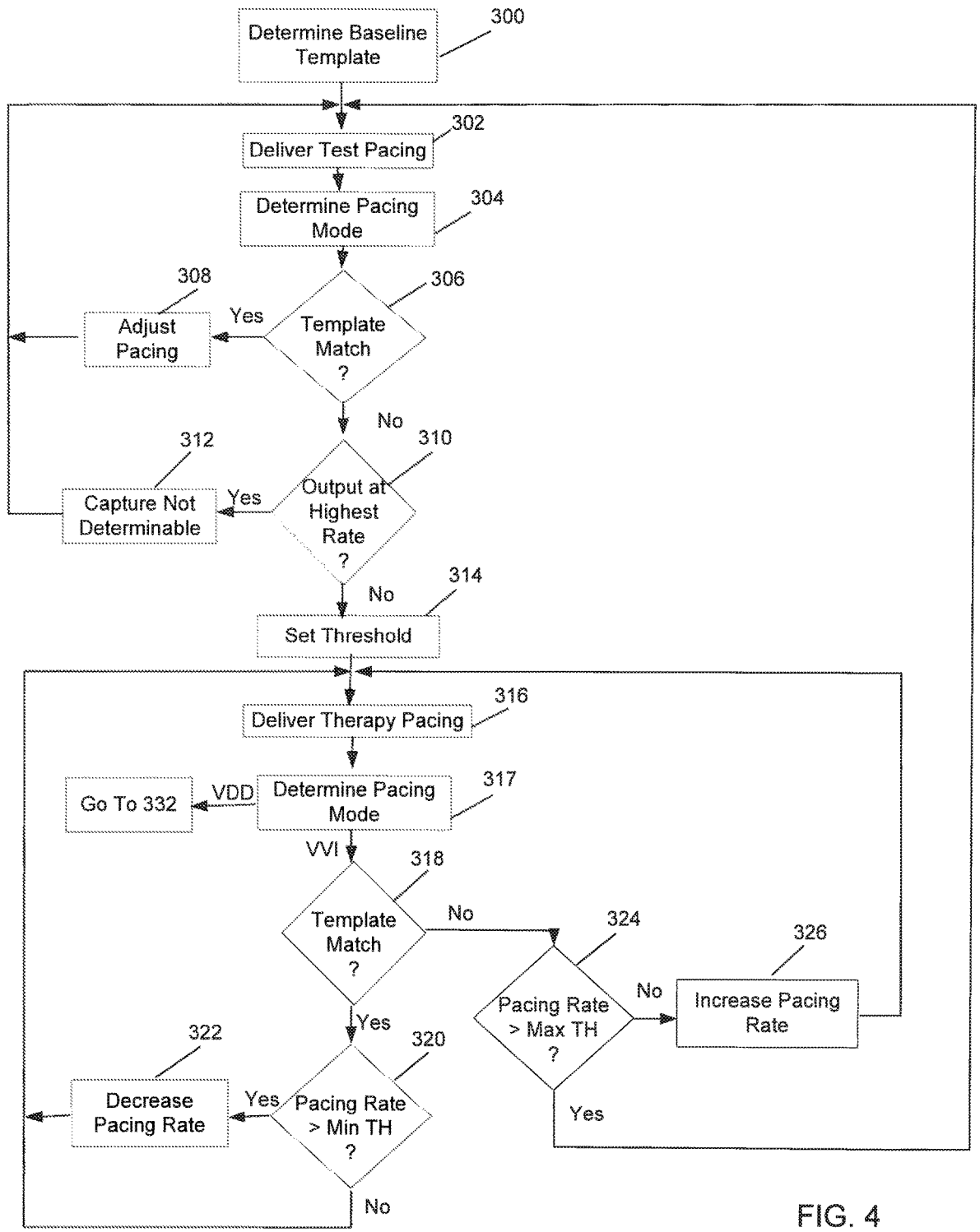
FIG. 4 is a flowchart of a method of delivering left ventricular pacing during cardiac resynchronization therapy in a medical device and medical device system, according to an embodiment of the present disclosure.

FIG. 4 is a flowchart of a method of delivering left ventricular pacing during cardiac resynchronization therapy in a medical device and medical device system, according to an embodiment of the present disclosure. As illustrated in FIG. 4, according to an embodiment of the present disclosure, during delivery of ventricular pacing associated with cardiac resynchronization therapy by the therapy delivery device 12, the sensing device 14 initially performs a capture management analysis routine for determining whether or not the pacing output associated with ventricular pacing therapy delivered by the therapy delivery device 12 effectively captures the patient's heart. In order to perform the capture management analysis routine, a baseline intrinsic template associated with an intrinsic beat sensed during normal activity of the heart when the sensed beat includes both a P-wave portion and an R-wave portion is determined, Block 300.

Once the baseline intrinsic template is determined, the sensing device 14 emits a trigger signal via the trigger signal emitting device 114, which is then received by the therapy delivery device 12, and instructs the therapy delivery device 12 to begin delivering the test ventricular pacing therapy for the baseline intrinsic template, Block 302. The trigger signal emitted by the sensing device 14 initially instructs the therapy delivery device 12 to deliver the left ventricular pacing therapy using a short atrioventricular delay, such as between 10 ms and 18 ms, and the highest available ventricular pacing output, such as 8 volts, for example. Once the test ventricular pacing therapy is delivered by the therapy delivery device 12, Block 302, the sensing device 14 senses the resulting subcutaneous cardiac signal via far-field sensors 16 and 18, and identifies a subsequent beat within the sensed signal resulting from the delivered ventricular pacing therapy.

Depending on the cardiac signal being received, the sensing device 14 may operate in either a VDD mode, where pacing occurs in the ventricle, and the sensed subcutaneous cardiac signal is associated with both an atrial and a ventricular signal, and a VVI mode, where pacing occurs in the ventricle, and the sensed subcutaneous cardiac signal is associated with only a ventricular signal, such as when atrial fibrillation is occurring and therefore the P-wave portion of the subcutaneous cardiac signal is no longer sensed by the sensing device 14. When in the VDD mode, where both a P-wave and an R-wave are included in the sensed subcutaneous cardiac signal, the sensing device 14 times the delivery of the pacing therapy based on the sensed P-wave, so that pacing therapy is delivered by the therapy delivery device 12 each time a P-wave is sensed by the sensing device 14. When in the VVI mode, the sensing device drives the delivery of the pacing therapy based on a predetermined pacing rate, such as 80 ms for example, so that pacing is delivered by the therapy delivery device 14 every 80 ms. In this way, when in the VDD mode, the sensing device 14 senses a subcutaneous cardiac signal associated with both the atrium and the ventricle, and when in the VVI mode, the sensing device 14 senses a subcutaneous cardiac signal associated only with the ventricle.

If, while in the VDD mode, the subcutaneous cardiac signal sensed by sensing device 14 no longer includes a discernable P-wave portion of the signal, such as during an episode of atrial fibrillation, the sensing device 14 switches from the VDD mode to the VVI mode, so that delivery of the pacing is driven by the predetermined pacing rate rather than a sensed P-wave. In the same way, if, while in the VVI mode, the cardiac signal sensed by the sensing device 14 includes a P-wave portion of the signal along with the R-wave portion, the sensing device 14 switches from the VVI mode to the VDD mode, so that delivery of the pacing therapy is timed based on the sensed P-wave.

Therefore, the sensing device 14 determines, based on whether the subsequent sensed beat includes both a P-wave and an R-wave portion, which pacing mode is being utilized, Block 304, and therefore which template is to be utilized for the subsequently sensed subcutaneous signal. For example, according to one embodiment, if the subsequently sensed signal includes both a P-wave portion and an R-wave portion, and therefore a VDD pacing mode is determined in Block 304, the sensing device 14 sets a timing window for the subsequently sensed subcutaneous signal that is to be compared to a timing window of the baseline intrinsic template using a P-wave offset, as described below in FIG. 5A. On the other hand, if the subsequently sensed beat does not include a P-wave portion, and therefore a VVI mode is determined in Block 304, the sensing device 14 sets a timing window for the subsequently sensed subcutaneous signal that is to be compared to a timing window of the baseline intrinsic template based on timing of the ventricular pacing event rather than the P-wave, as described below in FIG. 5B.

The sensing device 12 compares the subsequent beat to the chosen stored baseline intrinsic template to determine whether or not the sensed beat resulting from the delivered ventricular pacing therapy matches the template, Block 306, and therefore whether or not the delivered ventricular pacing therapy is effective at capturing the patient's heart. In particular, for example, the sensing device 14 determines whether there is a template match between the subsequently sensed beat resulting from the delivered pacing and the baseline intrinsic template associated with an intrinsic beat. The determination of whether there is a template match may be made, for example, by calculating a correlation coefficient based on a point-by-point comparison of the sampled signal and the stored baseline intrinsic template, and comparing the correlation coefficient to a predetermined correlation coefficient threshold. Calculation of a correlation coefficient may be performed, for example, as generally described in U.S. Pat. No. 5,193,550 issued to Duffin, incorporated herein by reference in its entirety. According to another embodiment, the determination of whether there is a template match may be made, for example, by determining whether a peak-to-peak amplitude of the template and the current sensed beat is less than a predetermined amplitude. Yet another embodiment may involve comparison of wavelet-transformations of sampled signal and the stored template and compute a match-score as an index of similarity between ordered wavelet coefficients of the signal and the template, as generally described in U.S. Pat. No. 6,393,316 issued to Gillberg, incorporated herein by reference in its entirety.

Figure 5A:
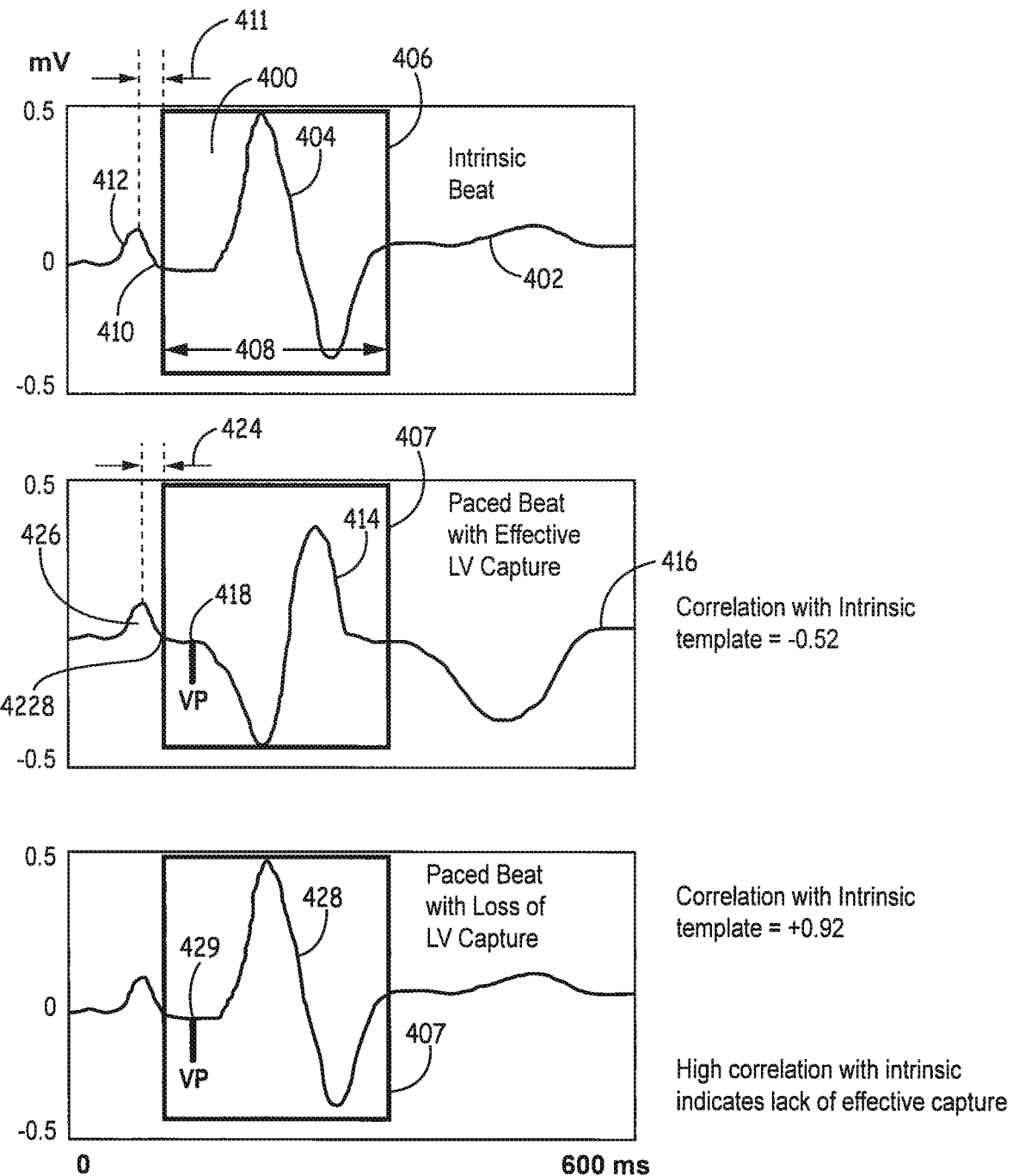
FIG. 5A is a schematic diagram illustrating deliver of left ventricular pacing during cardiac resynchronization therapy in a medical device and medical device system, according to an embodiment of the present disclosure.

FIG. 5A is a schematic diagram illustrating deliver of left ventricular pacing during cardiac resynchronization therapy in a medical device and medical device system, according to an embodiment of the present disclosure. As illustrated in FIG. 5, in order to determine the baseline intrinsic template 400 (Block 300 of FIG. 4) associated with a normal intrinsic beat, the sensing device 12 senses a subcutaneous cardiac signal 402 via subcutaneous electrodes 16 and 18 during a period of time that ventricular pacing therapy is not being delivered by the therapy delivery device 12. Once a QRS complex, or R-wave 404 of the sensed cardiac signal 402 is determined to occur, the sensing device 14 determines a timing window 406 having a predetermined width 408, such as 200 ms, for example, and a window starting point 410 located a predetermined P-wave offset 411 distance, such as 40 ms for example, from a corresponding P-wave 412 occurring prior to the sensed R-wave 404 of the QRS complex.

As illustrated in FIG. 5A, when the sensing device 14 senses both a P-wave portion 426 and an R-wave portion 414 in the subcutaneous signal 416 sensed as a result of a ventricular pace 418 being delivered, and therefore determines in Block 304 that the device is in the VVD mode, a timing window 407 associated with the R-wave portion 414 is determined and compared to the timing window 406 of the baseline intrinsic template 400, and a resulting correlation coefficient is determined based on the comparison. In particular, as illustrated in FIG. 5, according to one embodiment, during the determination of the timing window 407 for the resulting paced beat 414, the sensing device 14 determines the timing window 407 as having a window starting point 422 located the predetermined P-wave offset distance 424 from the P-wave 426 and extending the predetermined width 420, i.e., 200 ms, from the starting point 422.

According to the present disclosure, a subsequently sensed beat associated with a sensed subcutaneous cardiac signal and determined by the sensing device 14 to have a high correlation with the baseline intrinsic template indicates that the ventricular pacing therapy delivered by the therapy delivery device 12 does not effectively capture the heart. On the other hand, a determination that the sensed beat does not have a high correlation with the baseline intrinsic template indicates that the delivered ventricular pacing therapy does effectively capture the heart. According to one embodiment, a subsequently sensed beat is determined to be correlated with the baseline intrinsic template 400 if the correlation of the beat to the template is greater than a predetermined correlation threshold, such as 0.75 for example. A correlation coefficient greater than a certain threshold value is an indicator of match between sampled signal and intrinsic template. Exemplary values of threshold may be 0.6, 0.65, 0.75, 0.8. 0.85, 0.9, 0.95, for example.

Therefore, as illustrated in the exemplary schematic diagram of FIG. 5A, when a subsequently sensed beat or R-wave, such as R-wave 414 in FIG. 5, sensed by the sensing device 14 during delivery of the ventricular pacing therapy Vp 418 by the therapy delivery device 12 is determined to be less than the correlation threshold and therefore not to be highly correlated with the baseline intrinsic template 400, i.e., the correlation of the beat 414 is determined to be −0.52, the paced beat 414 associated with the delivered ventricular pacing therapy indicates effective capture of the heart. On the other hand, when a subsequently sensed beat or R-wave, such as R-wave 428 in FIG. 5 for example, sensed during delivery of the ventricular pacing therapy Vp 429 is determined not to be less than the correlation threshold and therefore highly correlated with the baseline intrinsic template 400, i.e., the correlation of the beat 428 is determined to be +0.92, the paced beat 428 associated with the delivered ventricular pacing therapy indicates ineffective capture of the heart, or loss of capture of the heart.

Figure 5B:
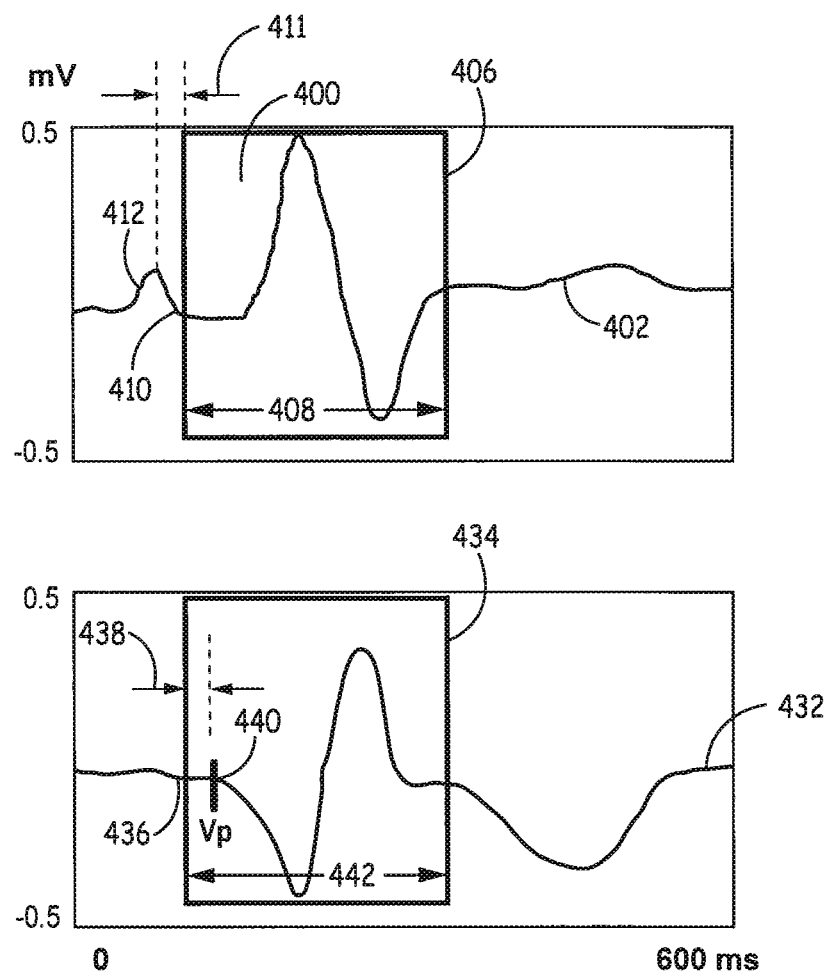
FIG. 5B is a schematic diagram illustrating delivery of left ventricular pacing during cardiac resynchronization therapy in a medical device and medical device system, according to an embodiment of the present disclosure.

FIG. 5B is a schematic diagram illustrating delivery of left ventricular pacing during cardiac resynchronization therapy in a medical device and medical device system, according to an embodiment of the present disclosure. As illustrated in FIG. 5B, when the sensing device 14 does not sense a P-wave portion and senses only an R-wave portion 430 in the subcutaneous signal 432 sensed as a result of a ventricular pace 434 being delivered, and therefore determines in Block 304 that the device is in the VVI mode, a timing window 434 associated with the R-wave portion 430 is determined as having a window starting point 436 located a predetermined V-pace offset distance 438, such as 40 ms for example, from a delivered ventricular pace 440 and extending the predetermined width 442, i.e., 200 ms, from the starting point 436. The timing window 434 is then compared to the timing window 406 of the baseline intrinsic template 400, after aligning the sampled signal with the intrinsic baseline template 400 based on the matching of fiducial points defined by the first change of sign of the slope with amplitude above a certain level (e.g. greater than 0.5 mV), the most dominant peak or valley, or the slope crossing a certain threshold, for example, and a resulting correlation coefficient is determined based on the comparison.

According to another embodiment, the timing window associated with the subsequently sensed beat resulting from the delivered pacing therapy may be set using the window starting point located the predetermined V-pace offset distance from a delivered ventricular pace both when in the VDD mode and the VVVI mode. As a result, the need for the sensing device 14 to determine whether the device is in the VDD mode or the VVI mode, Block 304 of FIG. 4, may be omitted.

Returning to FIG. 4, therefore, if the ventricular pacing therapy is determined to match the baseline intrinsic template, Yes in Block 306, indicating that a lack of effective pacing or loss of capture is determined to occur, the sensing device 14 adjusts the pacing output, Block 308, and sends the trigger signal to the therapy delivery device 12 instructing the therapy delivery device 12 to deliver the ventricular pacing therapy using the adjusted pacing output. The therapy delivery device 12 receives the trigger signal and delivers the test ventricular pacing therapy using the adjusted pacing output, Block 302, and the sensing device 14 then repeats the comparison of a resulting subsequent beat, sensed by the sensing device 14 during delivery of the test ventricular pacing therapy at the adjusted pacing output by the therapy delivery device 12, to the baseline intrinsic template, Block 302. According to one embodiment, during the adjusting of the pacing output in Block 308, the sensing device 14 may decrement the pacing output by a predetermined amount, such as 0.5 volts for example.

If the beat is determined not to match the baseline intrinsic template, No in Block 306, and therefore effective ventricular pacing therapy or capture is determined to occur, the sensing device 14 determines whether the current pacing output is set as the highest rate, Block 310. If the current pacing output is set at the highest rate, Yes in Block 310, the sensing device 14 determines that left ventricular capture is not currently determinable, Block 312, and the therapy delivery device 12 continues delivering the test ventricular pacing therapy, Block 302. If the current pacing output is not set at the highest rate, No in Block 310, the sensing device 14 sets the pacing output threshold equal to the current pacing output plus a predetermined delta, Block 314. Exemplary predetermined deltas may be 0.5V, 1.V, 1.5 V or 2.0V above the threshold pacing output voltage.

Once the pacing output threshold is determined in Block 314, the sensing device 14 emits a trigger signal that is then received by the therapy delivery device 12 and instructs the therapy delivery device 12 to deliver ventricular pacing therapy using the set pacing output threshold, Block 314, and an initial or predetermined pacing rate. The pacing rate may be programmable, and exemplary initial pacing rates may be 40 bpm, 45 bpm, 50 bpm, 55 bpm, 60 bpm, 65 bpm, 70 bpm, 75 bpm, 80 bpm, 90 bpm, 95 bpm, 100 bpm, 105 bpm, 110 bpm. The sensing device 14 senses the subcutaneous signal via electrodes 16 and 18 resulting from the delivered ventricular pacing therapy and determines, based on whether the subsequent sensed beat includes both a P-wave and an R-wave portion, which pacing mode is being utilized, Block 317, and therefore how the sensing window for the subsequently sensed subcutaneous signal is determined, as described above. For example, according to one embodiment, if the subsequently sensed signal includes both a P-wave portion and an R-wave portion, and therefore a VDD pacing mode is determined in Block 317, the sensing device 14 sets a timing window for the subsequently sensed subcutaneous signal that is to be compared to a timing window of the baseline intrinsic template using a P-wave offset, as above in FIG. 5A. On the other hand, if the subsequently sensed beat does not include a P-wave portion, and therefore a VVI mode is determined in Block 317, the sensing device 14 sets a timing window for the subsequently sensed subcutaneous signal that is to be compared to a timing window of the baseline intrinsic template based on timing of the ventricular pacing event rather than the P-wave, as described above in FIG. 5B.

According to the present disclosure, if the sensing device 14 determines that the device is operating in the VDD in Block 317, then the sensing device 14 performs the template matching as described below in Block 332 of FIG. 6 and adjusts the atrioventricular delay associated with the delivered ventricular pacing, as described below in FIG. 6. If the sensing device 14 determines that the device is operating in the VVI mode, the sensing device 14 performs the template matching associated with Block 318 of FIG. 4 and adjusts the pacing rate associated with the delivered ventricular pacing. In particular, when in the VVI mode, the sensing device 14 determines the sensing window of the subsequently sensed signal using the V-wave offset 438, described above, and compares the subsequently sensed beat or R-wave with the baseline intrinsic template 400 to determine whether the sensed beat matches the baseline intrinsic template 400, Block 318, as described above.

If the sensed beat is determined to match the baseline intrinsic template, Yes in Block 318, indicating that a lack of effective pacing or loss of capture is determined to occur, the sensing device 14 determines whether a pacing rate associated with the delivered ventricular pacing therapy is greater than a minimum pacing rate threshold, Block 320. The minimum pacing rate threshold may be set as the minimum programmable pacing rate plus a predetermined delta, such as 2 beats per minute, for example. An exemplary minimum rate may be 40 bpm, 45 bpm, 50 bpm, 55 bpm, or 60 bpm, for example.

If the pacing rate associated with the delivered ventricular pacing therapy is determined by the sensing device 14 to be greater than the minimum pacing rate threshold, Yes in Block 320, the sensing device 14 reduces the pacing rate by a predetermined amount, such as 2 beats per minute, for example, and emits a trigger signal via the trigger signal emitting device 114 instructing the therapy delivery device 12 to adjust the pacing rate of the delivered ventricular pacing therapy to the adjusted rate, Block 322, during subsequent delivery of the ventricular pacing therapy, Block 316 and the process continues as described above using the adjusted pacing rate. If the pacing rate associated with the delivered ventricular pacing therapy is determined by the sensing device 14 not to be greater than the minimum pacing rate threshold, No in Block 320, no changes are made to the delivered therapy and the delivery of the ventricular pacing therapy by the therapy delivery device 12 continues at the current pacing rate.

If the ventricular pacing therapy does not match the baseline intrinsic template, No in Block 318, indicating that effective pacing or capture is determined to occur as a result of the delivered ventricular pacing therapy, the sensing device 14 determines whether a pacing rate associated with the delivered ventricular pacing therapy is greater than a maximum pacing rate threshold, Block 324. The maximum pacing rate threshold may be set as the maximum programmable pacing rate minus a predetermined delta, such as 2 beats per minute, for example. An exemplary maximum rate may be 100 bpm, 105 bpm, 110 bpm, 115 bpm, 120 bpm, 125 bpm, or 130 bpm, for example.

If the pacing rate associated with the delivered ventricular pacing therapy is determined by the sensing device 14 not to be greater than the maximum pacing rate threshold, No in Block 324, the sensing device 14 adjusts the pacing rate by increasing the pacing rate by a predetermined amount, such as 2 beats per minute, for example, Block 326, and emits a trigger signal via the trigger signal emitting device 114 instructing the therapy delivery device 12 to adjust the pacing rate of the delivered ventricular pacing therapy to the adjusted rate, during subsequent delivery of the ventricular pacing therapy, Block 316 and the process continues using the adjusted pacing rate. If the pacing rate associated with the delivered ventricular pacing therapy is determined by the sensing device 14 to be greater than the maximum pacing rate threshold, Yes in Block 324, no changes are made to the delivered therapy and the left ventricular capture management process and determination of the pacing output threshold, Blocks 302-314, is repeated as described above.

Figure 6:
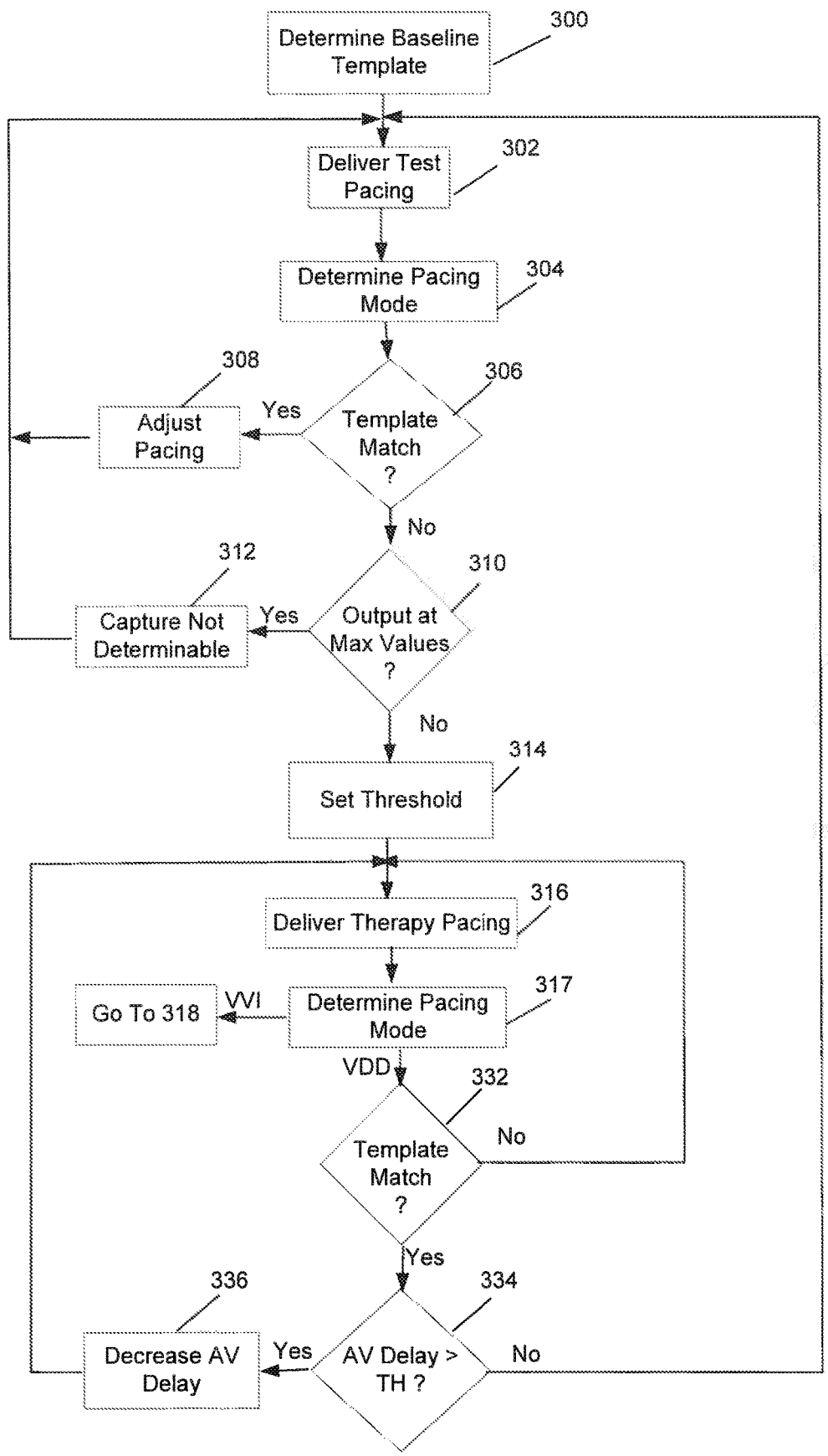
FIG. 6 is a flowchart of a method of delivering left ventricular pacing during cardiac resynchronization therapy in a medical device and medical device system, according to an embodiment of the present disclosure.

FIG. 6 is a flowchart of a method of delivering left ventricular pacing during cardiac resynchronization therapy in a medical device and medical device system, according to an embodiment of the present disclosure. The operation of Blocks 300-316 are similar as described in FIG. 4, and therefore will not be repeated for brevity sake. As illustrated in FIG. 6, when the device is determined to be in the VDD mode in Block 317 during delivery of the ventricular pacing therapy, Block 316, by the therapy delivery device 12, the sensing device 14 senses the resulting paced cardiac signal via subcutaneous electrodes 16 and 18, sets a timing window for the subsequently sensed subcutaneous signal that is to be compared to a timing window of the baseline intrinsic template using a P-wave offset, as described above in FIG. 5A, and compares the timing window of the subsequently sensed signal with the baseline intrinsic template window to determine whether the sensed beat matches the baseline intrinsic template, Block 332, indicating a lack of effective capture, as described above. If the R-wave matches the baseline intrinsic template, Yes in Block 332, indicating that a lack of effective pacing or loss of capture is determined to occur, the sensing device 14 determines whether the current set atrioventricular delay used during delivery of the pacing therapy is greater than a predetermined atrioventricular delay threshold, Block 334.

If the current set atrioventricular delay used during delivery of the pacing therapy is greater than the predetermined atrioventricular delay threshold, Yes in Block 334, the sensing device 14 adjusts the atrioventricular delay by a predetermined adjustment value. For example, according to one embodiment, the sensing device 14 adjusts the atrioventricular delay, Block 336, by decreasing the atrioventricular delay by a predetermined amount, such as 10 milliseconds, for example.

Once the atrioventricular delay is adjusted, Block 336, the sensing device emits a trigger signal via the trigger signal emitting device 114 instructing the therapy delivery device 12 to adjust the atrioventricular delay of the delivered ventricular pacing therapy to the adjusted atrioventricular delay of Block 336, during subsequent delivery of the ventricular pacing therapy, Block 316 and the process Blocks 318-336 is repeated. If the current set atrioventricular delay used during delivery of the pacing therapy is not greater than the predetermined atrioventricular delay threshold, No in Block 334, the atrioventricular delay is reset to its nominal or programmed value, and the left ventricular capture management process and determination of the pacing output threshold, Blocks 302-314, is repeated as described above.

The techniques described in this disclosure, including those attributed to the IMD, the programmer, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed:

1. A method of delivering left ventricular pacing in a medical device system, comprising:
   sensing a subcutaneous cardiac signal and emitting a trigger signal in response to the sensed cardiac signal;
   delivering the left ventricular pacing in response to the emitted trigger signal;
   employing the device system to determine whether the medical device system is in one of a VVD mode wherein the sensed subcutaneous cardiac signal is associated with both an atrial and a ventricular signal and a VVI mode wherein the sensed subcutaneous cardiac signal is associated with only a ventricular signal;
   employing the device system to determine whether the delivered left ventricular pacing captures the left ventricle;
   employing the device system to determine whether to adjust a pacing parameter in response to the determination of whether the device system is in one of the VVD mode and the VVI mode and the determination of whether the delivered left ventricular pacing captures the left ventricle; and
   delivering the left ventricular pacing in response to determining whether to adjust the pacing parameter; and further comprising:
   comparing a beat of a subcutaneous cardiac signal sensed in response to the left ventricular pacing to a baseline intrinsic template associated with a non-paced beat; and
   adjusting an atrioventricular delay of the left ventricular pacing in response to the comparing; and further comprising:
   employing the device system to determine a correlation between the beat and a baseline intrinsic template;
   employing the device system to determine whether the correlation is greater than a correlation threshold;
   employing the device system to determine whether the atrial ventricular delay is greater than an atrioventricular delay threshold;
   adjusting the atrioventricular delay of the ventricular pacing therapy in response to both the correlation being greater than the correlation threshold and the atrial ventricular delay being greater than the atrioventricular delay threshold;
   delivering the adjusted left ventricular pacing; and wherein adjusting the atrioventricular delay comprises decreasing the atrioventricular delay.

2. A method of delivering left ventricular pacing in a medical device system, comprising:
sensing a subcutaneous cardiac signal and emitting a trigger signal in response to the sensed cardiac signal;
delivering the left ventricular pacing in response to the emitted trigger signal;
employing the device system to determine whether the medical device system is in one of a VVD mode wherein the sensed subcutaneous cardiac signal is associated with both an atrial and a ventricular signal and a VVI mode wherein the sensed subcutaneous cardiac signal is associated with only a ventricular signal;
employing the device system to determine whether the delivered left ventricular pacing captures the left ventricle;
employing the device system to determine whether to adjust a pacing parameter in response to the determination of whether the device system is in one of the VVD mode and the VVI mode and the determination of whether the delivered left ventricular pacing captures the left ventricle; and
delivering the left ventricular pacing in response to determining whether to adjust the pacing parameter; and further comprising:
comparing a beat of a subcutaneous cardiac signal sensed in response to the left ventricular pacing to a baseline intrinsic template associated with a non-paced beat; and
adjusting an atrioventricular delay of the left ventricular pacing in response to the comparing; and further comprising:
employing the device system to determine a correlation between the beat and a baseline intrinsic template;
employing the device system to determine whether the correlation is greater than a correlation threshold;
employing the device system to determine whether the atrial ventricular delay is greater than an atrioventricular delay threshold;
adjusting the atrioventricular delay of the ventricular pacing therapy in response to both the correlation being greater than the correlation threshold and the atrial ventricular delay being greater than the atrioventricular delay threshold;
delivering the adjusted left ventricular pacing;
employing the device system to determine, in response to response to the correlation being greater than the correlation threshold and the atrial ventricular delay not being greater than the atrioventricular delay threshold, whether subsequently delivered left ventricular pacing captures the left ventricle; and
adjusting a pacing output of the left ventricular pacing in response to the subsequently delivered ventricular pacing capturing the left ventricle.

3. A medical device system for delivery ventricular pacing, comprising:
a subcutaneous sensing device comprising a subcutaneous electrode to sense a subcutaneous cardiac signal and an emitting device to emit a trigger signal in response to the sensed cardiac signal;
an intracardiac therapy delivery device to deliver the left ventricular pacing in response to the emitted trigger signal; and
a processor configured to determine whether the medical device system is in one of a VVD mode wherein the sensed subcutaneous cardiac signal is associated with both an atrial and a ventricular signal and a VVI mode wherein the sensed subcutaneous cardiac signal is associated with only a ventricular signal, determine whether the delivered left ventricular pacing captures the left ventricle, determine whether to adjust a pacing parameter in response to the determination of whether the device system is in one of the VVD pacing mode and the VVI pacing mode and the determination of whether the delivered left ventricular pacing captures the left ventricle, and deliver the left ventricular pacing in response to determining whether to adjust the pacing parameter;
wherein the processor is configured to compare a beat of a subcutaneous cardiac signal sensed in response to the left ventricular pacing to a baseline intrinsic template associated with a non-paced beat, and adjust an atrioventricular delay of the left ventricular pacing in response to the comparing: wherein the processor is configured to determine a correlation between the beat and a baseline intrinsic template, determine whether the correlation is greater than a correlation threshold, determine whether the atrial ventricular delay is greater than an atrioventricular delay threshold, adjust the atrioventricular delay of the ventricular pacing therapy in response to both the correlation being greater than the correlation threshold and the atrial ventricular delay being greater than the atrioventricular delay threshold, and deliver the adjusted left ventricular pacing; and
wherein the processor is configured to determine, in response to response to the correlation being greater than the correlation threshold and the atrial ventricular delay not being greater than the atrioventricular delay threshold, whether subsequently delivered left ventricular pacing captures the left ventricle, and adjust a pacing output of the left ventricular pacing in response to the subsequently delivered ventricular pacing capturing the left ventricle.

4. The medical device system of claim 3, wherein the processor is configured to compare a beat of a subcutaneous cardiac signal sensed in response to the left ventricular pacing to a baseline intrinsic template associated with a non-paced beat and decrease the atrioventricular delay in response to the correlation being greater than a correlation threshold.

5. A medical device system for delivery ventricular pacing, comprising:
a subcutaneous sensing device comprising a subcutaneous electrode to sense a subcutaneous cardiac signal and an emitting device to emit a trigger signal in response to the sensed cardiac signal;
an intracardiac therapy delivery device to deliver the left ventricular pacing in response to the emitted trigger signal; and
a processor configured to determine whether the medical device system is in one of a VVD mode-wherein the sensed subcutaneous cardiac signal is associated with both an atrial and a ventricular signal and a VVI mode wherein the sensed subcutaneous cardiac signal is associated with only a ventricular signal, determine whether the delivered left ventricular pacing captures the left ventricle, determine whether to adjust a pacing parameter in response to the determination of whether the device system is in one of the VVD pacing mode and the VVI pacing mode and the determination of whether the delivered left ventricular pacing captures the left ventricle, and deliver the left ventricular pacing in response to determining whether to adjust the pacing parameter;

wherein the processor is configured to compare a beat of a subcutaneous cardiac signal sensed subsequent to the left ventricular pacing to a baseline intrinsic template associated with a non-paced beat, and adjust a pacing rate of the left ventricular pacing in response to the comparing;

wherein the processor is configured to determine a correlation between the beat and a baseline intrinsic template, perform a first adjusting of the pacing rate in response to the correlation being greater than a correlation threshold, and perform a second adjusting of the pacing rate, different from the first adjusting, in response to the correlation being greater than the correlation threshold; and wherein the processor is configured to determine, in response to the correlation being greater than the correlation threshold, whether a pacing rate of the ventricular pacing is greater than a minimum pacing rate threshold, and decrease the pacing rate in response to the pacing rate being greater than the minimum pacing rate threshold.

6. The medical device system of claim 5, wherein the processor is configured to determine, in response to both the correlation not being greater than the correlation threshold and the pacing rate being greater than the maximum pacing rate threshold, whether subsequently delivered left ventricular pacing captures the left ventricle, and adjust a pacing output of the left ventricular pacing in response to the subsequently delivered ventricular pacing capturing the left ventricle.

7. The medical device system of claim 5, wherein the processor is configured to determine, in response to the correlation not being greater than the correlation threshold, whether a pacing rate of the ventricular pacing is greater than a maximum pacing rate threshold, and increase the pacing rate in response to the pacing rate not being greater than the maximum pacing rate threshold.

8. A subcutaneous medical device for delivering left ventricular pacing therapy, comprising:

a subcutaneous sensing device comprising a subcutaneous electrode to sense a subcutaneous cardiac signal and an emitting device to emit a trigger signal in response to the sensed cardiac signal; and a processor configured to determine whether the medical device system is in one of a VVD mode wherein the sensed subcutaneous cardiac signal is associated with both an atrial and a ventricular signal and a VVI mode wherein the sensed subcutaneous cardiac signal is associated with only a ventricular signal, determine whether the delivered left ventricular pacing captures the left ventricle, determine whether to adjust a pacing parameter in response to the determination of whether the device system is in one of the VVD mode and the VVI mode and the determination of whether the delivered left ventricular pacing captures the left ventricle, and emit the trigger signal to deliver the left ventricular pacing in response to determining whether to adjust the pacing parameter wherein the processor is configured to compare a beat of a subcutaneous cardiac signal sensed subsequent to the left ventricular pacing to a baseline intrinsic template associated with a non-paced beat, and adjust a pacing rate of the left ventricular pacing in response to the comparing;

wherein the processor is configured to determine a correlation between the beat and a baseline intrinsic template, perform a first adjusting of the pacing rate in response to the correlation being greater than a correlation threshold, and perform a second adjusting of the pacing rate, different from the first adjusting, in response to the correlation being greater than the correlation threshold; and wherein the processor is configured to determine, in response to the correlation being greater than the correlation threshold, whether a pacing rate of the ventricular pacing is greater than a minimum pacing rate threshold, and decrease the pacing rate in response to the pacing rate being greater than the minimum pacing rate threshold.

9. The subcutaneous medical device of claim 8, wherein the processor is configured to determine, in response to both the correlation not being greater than the correlation threshold and the pacing rate being greater than the maximum pacing rate threshold, whether subsequently delivered left ventricular pacing captures the left ventricle, and adjust a pacing output of the left ventricular pacing in response to the subsequently delivered ventricular pacing capturing the left ventricle.

10. The subcutaneous medical device of claim 8, wherein the processor is configured to determine, in response to the correlation not being greater than the correlation threshold, whether a pacing rate of the ventricular pacing is greater than a maximum pacing rate threshold, and increase the pacing rate in response to the pacing rate not being greater than the maximum pacing rate threshold.

11. A medical device system for delivery ventricular pacing, comprising:

a subcutaneous sensing device comprising a subcutaneous electrode to sense a subcutaneous cardiac signal and an emitting device to emit a trigger signal in response to the sensed cardiac signal;

an intracardiac therapy delivery device to deliver the left ventricular pacing in response to the emitted trigger signal; and a processor configured to determine whether the medical device system is in one of a VVD mode-wherein the sensed subcutaneous cardiac signal is associated with both an atrial and a ventricular signal and a VVI mode wherein the sensed subcutaneous cardiac signal is associated with only a ventricular signal, determine whether the delivered left ventricular pacing captures the left ventricle, determine whether to adjust a pacing parameter in response to the determination of whether the device system is in one of the VVD pacing mode and the VVI pacing mode and the determination of whether the delivered left ventricular pacing captures the left ventricle, and deliver the left ventricular pacing in response to determining whether to adjust the pacing parameter;

wherein the processor is configured to compare a beat of a subcutaneous cardiac signal sensed subsequent to the left ventricular pacing to a baseline intrinsic template associated with a non-paced beat, and adjust a pacing rate of the left ventricular pacing in response to the comparing;

wherein the processor is configured to determine a correlation between the beat and a baseline intrinsic template, perform a first adjusting of the pacing rate in response to the correlation being greater than a correlation threshold, and perform a second adjusting of the pacing rate, different from the first adjusting, in response to the correlation being greater than the correlation threshold; and wherein the processor is configured to determine, in response to the correlation not being greater than the correlation threshold, whether a pacing rate of the ventricular pacing is greater than a maximum pacing rate threshold, and increase the pacing rate in response to the pacing rate not being greater than the maximum pacing rate threshold.

12. A subcutaneous medical device for delivering left ventricular pacing therapy, comprising:

a subcutaneous sensing device comprising a subcutaneous electrode to sense a subcutaneous cardiac signal and an emitting device to emit a trigger signal in response to the sensed cardiac signal; and a processor configured to determine whether the medical device system is in one of a VVD mode wherein the sensed subcutaneous cardiac signal is associated with both an atrial and a ventricular signal and a VVI mode wherein the sensed subcutaneous cardiac signal is associated with only a ventricular signal, determine whether the delivered left ventricular pacing captures the left ventricle, determine whether to adjust a pacing parameter in response to the determination of whether the device system is in one of the VVD mode and the VVI mode and the determination of whether the delivered left ventricular pacing captures the left ventricle, and emit the trigger signal to deliver the left ventricular pacing in response to determining whether to adjust the pacing parameter; and wherein the processor is configured to determine a correlation between the beat and a baseline intrinsic template, determine whether the correlation is greater than a correlation threshold, determine whether the atrial ventricular delay is greater than an atrioventricular delay threshold, adjust the atrioventricular delay of the ventricular pacing therapy in response to both the correlation being greater than the correlation threshold and the atrial ventricular delay being greater than the atrioventricular delay threshold, and deliver the adjusted left ventricular pacing; and wherein the processor is configured to determine, in response to response to the correlation being greater than the correlation threshold and the atrial ventricular delay not being greater than the atrioventricular delay threshold, whether subsequently delivered left ventricular pacing captures the left ventricle, and adjust a pacing output of the left ventricular pacing in response to the subsequently delivered ventricular pacing capturing the left ventricle.

13. A subcutaneous medical device for delivering left ventricular pacing therapy, comprising:

a subcutaneous sensing device comprising a subcutaneous electrode to sense a subcutaneous cardiac signal and an emitting device to emit a trigger signal in response to the sensed cardiac signal; and a processor configured to determine whether the medical device system is in one of a VVD mode wherein the sensed subcutaneous cardiac signal is associated with both an atrial and a ventricular signal and a VVI mode wherein the sensed subcutaneous cardiac signal is associated with only a ventricular signal, determine whether the delivered left ventricular pacing captures the left ventricle, determine whether to adjust a pacing parameter in response to the determination of whether the device system is in one of the VVD mode and the VVI mode and the determination of whether the delivered left ventricular pacing captures the left ventricle, and emit the trigger signal to deliver the left ventricular pacing in response to determining whether to adjust the pacing parameter wherein the processor is configured to compare a beat of a subcutaneous cardiac signal sensed subsequent to the left ventricular pacing to a baseline intrinsic template associated with a non-paced beat, and adjust a pacing rate of the left ventricular pacing in response to the comparing;

wherein the processor is configured to determine a correlation between the beat and a baseline intrinsic template, perform a first adjusting of the pacing rate in response to the correlation being greater than a correlation threshold, and perform a second adjusting of the pacing rate, different from the first adjusting, in response to the correlation being greater than the correlation threshold; and wherein the processor is configured to determine, in response to the correlation not being greater than the correlation threshold, whether a pacing rate of the ventricular pacing is greater than a maximum pacing rate threshold, and increase the pacing rate in response to the pacing rate not being greater than the maximum pacing rate threshold.

\* \* \* \* \*